(12) United States Patent
Koenemann et al.

(10) Patent No.: US 7,678,907 B2
(45) Date of Patent: Mar. 16, 2010

(54) HALOGENATION OF RYLEN-CARBOXIMIDES WITH ELEMENTARY HALOGEN IN A TWO-PHASE MIXTURE COMPRISING AN ORGANIC SOLVENT AND WATER, WHEREIN FORMED HALOGEN HYDROXIDE IS CONTINUOUSLY REMOVABLE FROM THE ORGANIC SOLVENT

(75) Inventors: Martin Koenemann, Mannheim (DE); Neil Gregory Pschirer, Mainz (DE)

(73) Assignee: BASF Aktiengessellschaft, Ludwigshafen (DE)

( * ) Notice: Subject to any disclaimer, the term of this patent is extended or adjusted under 35 U.S.C. 154(b) by 526 days.

(21) Appl. No.: 11/576,157

(22) PCT Filed: Sep. 28, 2005

(86) PCT No.: PCT/EP2005/010490

§ 371 (c)(1),
(2), (4) Date: Mar. 28, 2007

(87) PCT Pub. No.: WO2006/037539

PCT Pub. Date: Apr. 13, 2006

(65) Prior Publication Data

US 2008/0058526 A1 Mar. 6, 2008

(30) Foreign Application Priority Data

Oct. 5, 2004 (DE) ........................ 10 2004 048 729

(51) Int. Cl.
*C07D 221/18* (2006.01)
(52) U.S. Cl. ........................................ 546/36
(58) Field of Classification Search .................... 546/36
See application file for complete search history.

(56) References Cited

U.S. PATENT DOCUMENTS

| | | | |
|---|---|---|---|
| 4,667,036 A | 5/1987 | Iden et al. | |
| 4,845,223 A | 7/1989 | Seybold et al. | |
| 5,986,099 A | 11/1999 | Müllen et al. | |
| 6,124,458 A | 9/2000 | Müllen et al. | |
| 6,143,905 A | 11/2000 | Böhm et al. | |
| 6,326,494 B1 | 12/2001 | Böhm et al. | |
| 2005/0222416 A1 | 10/2005 | Bohm et al. | |

FOREIGN PATENT DOCUMENTS

| | | |
|---|---|---|
| DE | 25 19 790 | 11/1976 |
| DE | 159 066 | 2/1983 |
| DE | 3434059 | 3/1985 |
| EP | 0 227 980 | 7/1987 |
| SU | 392 064 | 7/1983 |
| WO | WO 96/22332 | 7/1996 |
| WO | WO 97/22607 | 6/1997 |
| WO | WO 03/104232 | 12/2003 |
| WO | WO 2006/037539 | 4/2006 |

OTHER PUBLICATIONS

Kin-ya Tomizaki, et al., "Practical Synthesis of Perylene-Monoimide Building Blocks that Possess Features Appropriate for Use in Porphyrin-Based Light-Harvesting Arrays," Tetrahedron, 59, (2003), 1191-1207.

*Primary Examiner*—Taofiq A Solola
(74) *Attorney, Agent, or Firm*—Oblon, Spivak, McClelland, Maier & Neustadt, L.L.P.

(57) ABSTRACT

A process for preparing halogenated rylenecarboximides of the general formula I

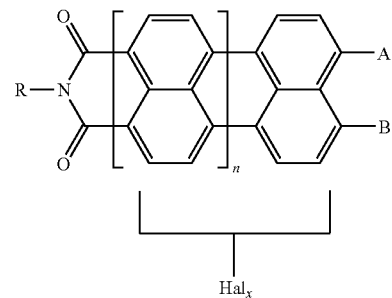

in which the variables are each defined as follows:
A, B together are an imide radical or, in the case that n is 1, A and B are also each Hal or one radical is Hal and the other radical is halogen;
R, R' are each independently hydrogen; optionally substituted alkyl, cycloalkyl, aryl or hetaryl;
Hal is chlorine, bromine or iodine;
n is 1, 2 or 3;
x is from 2 to 8,
by reacting a rylenecarboximide of the general formula II

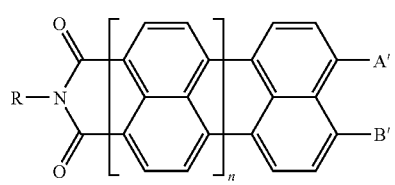

in which the A' and B' radicals together are an imide radical or, in the case that n is 1, are also each hydrogen
with elemental halogen in the presence of an inert organic solvent S1, which comprises continuously withdrawing the hydrogen halide formed in the course of the reaction from the solvent S1.

11 Claims, No Drawings

HALOGENATION OF RYLEN-CARBOXIMIDES WITH ELEMENTARY HALOGEN IN A TWO-PHASE MIXTURE COMPRISING AN ORGANIC SOLVENT AND WATER, WHEREIN FORMED HALOGEN HYDROXIDE IS CONTINUOUSLY REMOVABLE FROM THE ORGANIC SOLVENT

The present invention relates to a novel process for preparing halogenated rylenecarboximides of the general formula I

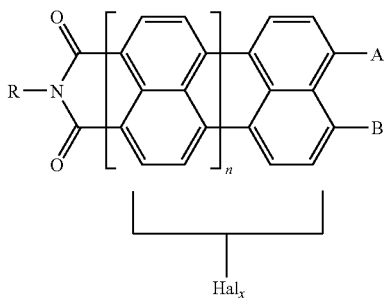

in which the variables are each defined as follows:

A, B together are an imide radical of the formula

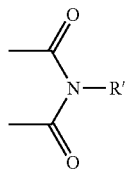

or, in the case that n is 1, A and B are each Hal or one radical is Hal and the other radical is hydrogen;

R, R' are each independently:

hydrogen;

(1) $C_1$-$C_{30}$-alkyl whose carbon chain may be interrupted by one or more —O—, —S—, —$NR^1$—, —N=$CR^1$—, —C≡C—, —$CR^1$=$CR^1$—, —CO—, —SO— and/or —$SO_2$— moieties and which may be mono- or polysubstituted by:

(i) $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(ii) aryl or hetaryl, to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$, —$POR^2R^3$, aryl and/or hetaryl, each of which may be substituted by $C_1$-$C_{18}$-alkyl, $C_1$-$C_{12}$-alkoxy, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iii) $C_3$-$C_8$-cycloalkyl whose carbon skeleton may be interrupted by one or more —O—, —S—, —$NR^1$—, —N=$CR^1$—, —$CR^1$=$CR^1$—, —CO—, —SO— and/or —$SO_2$— moieties and to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iv) a -U-aryl radical which may be mono- or polysubstituted by the above radicals specified as substituents for the aryl radicals (ii), where U is an —O—, —S—, —$NR^1$—, —CO—, —SO— and/or —$SO_2$— moiety;

(2) $C_3$-$C_8$-cycloalkyl, to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by the (i), (ii), (iii), (iv) radicals, and/or (v) $C_1$-$C_{30}$-alkyl whose carbon chain may be interrupted by one or more —O—, —S—, —$NR^1$—, —N=$CR^1$—, —C≡C—, —$CR^1$=$CR^1$—, —CO—, —SO— and/or —$SO_2$— moieties and which may be mono- or polysubstituted by: $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$, aryl and/or saturated or unsaturated $C_4$-$C_7$-cycloalkyl whose carbon skeleton may be interrupted by one or more —O—, —S—, —$NR^1$—, —N=$CR^1$—, —$CR^1$=$CR^1$—, —CO—, —SO— and/or —$SO_2$— moieties, where the aryl and cycloalkyl radicals may each be mono- or polysubstituted by $C_1$-$C_{18}$-alkyl and/or the above radicals specified as substituents for alkyl;

(3) aryl or hetaryl, to which may be fused further saturated or unsaturated 5- to 7-membered rings whose carbon skeleton may be interrupted by one or more —O—, —S—, —$NR^1$—, —N=$CR^1$—, —C≡C—, —$CR^1$=$CR^1$—, —CO—, —SO— and/or —$SO_2$— moieties, where the entire ring system may be substituted by the (i), (ii), (iii), (iv), (v) radicals, and/or aryl- and/or hetarylazo, each of which may be substituted by $C_1$-$C_{10}$-alkyl, $C_1$-$C_6$-alkoxy and/or cyano;

$R^1$ is hydrogen or $C_1$-$C_{18}$alkyl, where the $R^1$ radicals may be the same or different when they occur more than once;

$R^2$, $R^3$ are each independently hydrogen;

$C_1$-$C_{18}$-alkyl whose carbon chain may be interrupted by one or more —O—, —S—, —CO—, —SO— and/or —$SO_2$— moieties and which may be mono- or polysubstituted by $C_1$-$C_{12}$-alkoxy, $C_1$-$C_6$-alkylthio, hydroxyl, mercapto, halogen, cyano, nitro and/or —$COOR^1$;

aryl or hetaryl, to each of which may be fused further saturated or unsaturated 5- to 7-membered rings whose carbon skeleton may be interrupted by one or more —O—, —S—, —CO—, and/or —$SO_2$— moieties, where the entire ring system may be mono- or polysubstituted by $C_1$-$C_{12}$-alkyl and/or the above radicals specified as substituents for alkyl;

Hal is chlorine, bromine or iodine;

n is 1, 2 or 3;

x is from 2 to 8.

Halogenated rylenecarboximides, in particular brominated perylene-3,4-dicarboximides, terrylene-3,4:11,12-tetracarboximides and quaterrylene-3,4:13,14-tetracarboximides, are important intermediates in the synthesis of fluorescent dyes, infrared absorbers and pigment additives based on rylene. They are converted to the desired target compounds by nucleophilic substitution reactions (exchange of the bromine atoms, for example, for phenoxy radicals) and/or condensation reactions in the peri-position (formation of C—C bonds with hydrogen bromide elimination).

For the preparation of the brominated rylenecarboximides, the reaction of the rylenecarboximides unsubstituted in the rylene ring with elemental bromine in the absence of water in chlorinated hydrocarbons is already known. Typically, high dilution and high bromine excess and/or high temperature are employed. The large amounts of solvent are required in order to suppress undesired side reactions (bromination of aliphatic and aromatic radicals on the imide nitrogen atoms and uncontrolled bromination in the rylene ring) and to obtain the desired bromination products selectively.

For instance, WO-A-96/22332 describes the preparation of brominated perylene-3,4-dicarboximides and quaterrylene-3,4:13,14-tetracarboximides. Explicitly disclosed is the tri- or hexabromination of N-(2,6-diisopropylphenyl)perylene-3,4-dicarboximide and N,N'-bis(2,6-diisopropylphenyl)quaterrylene-3,4:13,14-tetracarboximide in 125 ml of chloroform/g of imide at a molar ratio of bromine to imide of 58.4:1 at 61° C.

WO-A-03/104232 relates to the bromination of terrylene-3,4:11,12-tetracarboximides. Explicitly disclosed is the tetra- and dibromidation of various terrylene-3,4:11,12-tetracarboximides in solvent amounts of from 70 to 100 ml/g of imide at a molar ratio of bromine to imide of 5 and 2.5:1 respectively, and temperatures of from 65 to 80° C. and from 60 to 65° C. respectively.

Although Tetrahedron 59, p. 1191-1207 (2003) describes the preparation of N-(2,5-di-tert-butylphenyl)tribromoperylene-3,4-dicarboximide by bromination in 30 ml of chloroform/g of imide at a molar ratio of bromine to imide of 15.7:1, it is not possible for selective bromination to proceed under these conditions. Accordingly, only a yield of 32% is achieved here after column chromatography.

For the preparation of halogenated perylene-3,4:9,10-tetracarboximides, alternative reaction routes are typically taken. For instance, the dibromo- and the tetrachloroimides may be obtained by reacting perylene-3,4:9,10-tetracarboxylic dianhydride with elemental bromine and chlorine respectively in 100% by weight sulfuric acid and subsequent imidation (WO-A-97/22607, and DE-A-25 19 790 and EP-A-227 980, respectively). Finally, DE-A-34 34 049 also describes the chlorination of the imides with sulfuryl chloride in nitrobenzene.

It is an object of the invention to make accessible relatively highly halogenated rylenecarboximides (i.e. comprising at least three halogen atoms in the molecule) with very high selectivity and in an advantageous manner from a process technology point of view, and in particular also to reduce the amount of solvent required for the halogenation.

Accordingly, a process has been found for preparing halogenated rylenecarboximides of the general formula I

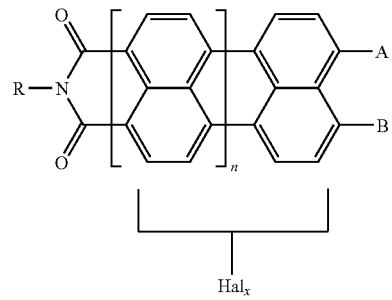

in which the variables are each defined as follows:

A, B together are an imide radical of the formula

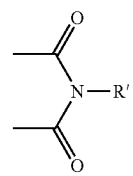

or, in the case that n is 1, A and B are also each Hal or one radical is Hal and the other radical is hydrogen;

R, R' are each independently:

hydrogen;

(1) $C_1$-$C_{30}$-alkyl whose carbon chain may be interrupted by one or more —O—, —S—, —NR$^1$—, —N═CR$^1$—, —C≡C—, —CR$^1$═CR$^1$—, —CO—, —SO— and/or —SO$_2$— moieties and which may be mono- or polysubstituted by:

(i) $C_1$-$C_{12}$-alkoxy, $C_1$-$C_6$-alkylthio, —C≡CR$^1$, —CR$^1$═CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(ii) aryl or hetaryl, to which may be fused further saturated or unsaturated 5- to 7-membered rings whose carbon skeleton may be interrupted by one or more —O—, —S—, —NR$^1$—, —N═CR$^1$—, —CR$^1$═CR$^1$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^1$, —CR$^1$═CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or hetaryl, each of which may be substituted by $C_1$-$C_{18}$-alkyl, $C_1$-$C_{12}$-alkoxy, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(iii) $C_3$-$C_8$-cycloalkyl whose carbon skeleton may be interrupted by one or more —O—, —S—, —NR$^1$—, —N═CR$^1$—, —CR$^1$═CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$—, —N═CR$^1$—, —CR$^1$═CR$^1$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(iv) a -U-aryl radical which may be mono- or polysubstituted by the above radicals specified as substituents for the aryl radicals (ii), where U is an —O—, —S—, —NR$^1$—, —CO—, —SO— and/or —SO$_2$— moiety;

(2) $C_3$-$C_8$-cycloalkyl, to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by the (i), (ii), (iii), (iv) radicals, and/or (v) $C_1$-$C_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by: $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —PR$^2$R$^3$, —POR$^2$R$^3$, aryl and/or saturated or unsaturated $C_4$-$C_7$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties, where the aryl and cycloalkyl radicals may each be mono- or polysubstituted by $C_1$-$C_{18}$-alkyl and/or the above radicals specified as substituents for alkyl;

(3) aryl or hetaryl, to which may be fused further saturated or unsaturated 5- to 7-membered rings whose carbon skeleton may be interrupted by one or more —O—, —S—, —NR$^1$—, —N=CR$^1$—, —C≡C—, —CR$^1$=CR$^1$—, —CO—, —SO— and/or —SO$_2$— moieties, where the entire ring system may be substituted by the (i), (ii), (iii), (iv), (v) radicals, and/or aryland/or hetarylazo, each of which may be substituted by $C_1$-$C_{10}$-alkyl, $C_1$-$C_6$-alkoxy and/or cyano;

R$^1$ is hydrogen or $C_1$-$C_{18}$alkyl, where the R$^1$ radicals may be the same or different when they occur more than once;

R$^2$, R$^3$ are each independently hydrogen;
$C_1$-$C_{18}$-alkyl whose carbon chain may be interrupted by one or more —O—, —S—, —CO—, —SO— and/or —SO$_2$— moieties and which may be mono- or polysubstituted by $C_1$-$C_{12}$-alkoxy, $C_1$-$C_6$-alkylthio, hydroxyl, mercapto, halogen, cyano, nitro and/or —COOR$^1$;
aryl or hetaryl, to each of which may be fused further saturated or unsaturated 5- to 7-membered rings whose carbon skeleton may be interrupted by one or more —O—, —S—, —CO—, —SO— and/or —SO$_2$— moieties, where the entire ring system may be mono- or polysubstituted by $C_1$-$C_{12}$-alkyl and/or the above radicals specified as substituents for alkyl;

Hal is chlorine, bromine or iodine;
n is 1, 2 or 3;
x is from 2 to 8, by reacting a rylenecarboximide of the general formula II

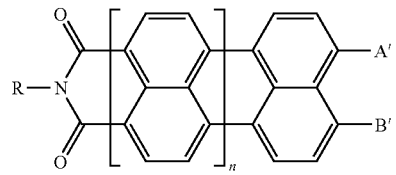

in which the A' and B' radicals together are an imide radical of the formula

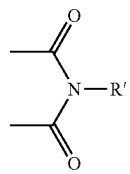

or, in the case that n is 1, are also each hydrogen with elemental halogen in the presence of an inert organic solvent S1, which comprises continuously withdrawing the hydrogen halide formed in the course of the reaction from the solvent S1.

The process according to the invention preferably finds use for preparing halogenated rylenecarboximides of the formula I in which the variables are each defined as follows:

R,R' are each independently hydrogen;
$C_1$-$C_{30}$-alkyl whose carbon chain may be interrupted by one or more —O—, —S—, —NR$^1$—, —CO— and/or —SO$_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and may comprise further heteroatoms and be aromatic;

$C_5$-$C_8$-cycloalkyl whose carbon skeleton may be interrupted by one or more —O—, —S— and/or —NR$^1$— moieties and/or which may be mono- or polysubstituted by $C_1$-$C_6$-alkyl;

aryl or hetaryl, each of which may be mono- or polysubstituted by $C_1$-$C_{18}$-alkyl, $C_1$-$C_6$-alkoxy, cyano, halogen, —CONHR$^2$, —SO$_2$R$^2$, —SO$_2$NR$^2{}_2$ and/or aryl- or hetarylazo, each of which may be substituted by $C_1$-$C_{10}$-alkyl, $C_1$-$C_6$-alkoxy or cyano;

R$^1$ is hydrogen or $C_1$-$C_6$-alkyl;
R$^2$ is hydrogen; $C_1$-$C_{18}$-alkyl; aryl or hetaryl, each of which may be substituted by $C_1$-$C_6$-alkyl, $C_1$-$C_6$-alkoxy, halogen, hydroxy, carboxy or cyano.

The removal of the hydrogen halide from the system increases the selectivity of the halogenation. It is no longer necessary to work in high dilution, so that the reaction is simplified on the industrial scale in particular, since the handling of large amounts of solvent becomes unnecessary.

In the process according to the invention, preference is given to withdrawing the hydrogen halide by contacting the solvent S1 with a solvent S2, by which the hydrogen halide formed is removed from the solvent S1, and in which the hydrogen halide dissolves better.

In addition, the solvent S2 should not mix with the solvent S1 (should form two phases) or should have a higher boiling point than the solvent S1 and be separable from it by distillation.

Suitable for the absorption of the hydrogen halide formed are in particular water, which is the preferred solvent in S2 also owing to the immiscibility with the organic solvents which are suitable as the reaction medium for halogenations, and to its high boiling point in comparison to these solvents.

In order to further increase the effectiveness of the removal of the hydrogen halide from the system, it is also possible if necessary, instead of pure water, to use aqueous solutions of oxidizing agents and/or bases which oxidize the hydrogen halide to halogen which is then available again for halogenation, or bind the hydrogen halide by acid-base reaction.

Suitable oxidizing agents are in particular oxidizing inorganic salts such as peroxodisulfates, nitrates, bromates, hypochlorites, chlorates, perchlorates and permanganates.

Suitable bases are in particular inorganic bases such as water-soluble alkali metal and alkaline earth metal hydroxides, alkali metal and alkaline earth metal carbonates, and alkali metal and alkaline earth metal hydrogencarbonates, in particular lithium hydroxide, carbonate and hydrogencarbonate, sodium hydroxide, carbonate and hydrogencarbonate, potassium hydroxide, carbonate and hydrogencarbonate, and magnesium hydroxide, carbonate and hydrogencarbonate.

Suitable inert organic solvents S1 for the process according to the invention are those compounds which are inert toward the halogens under the reaction conditions.

Among these solvents, preference is given to those which are immiscible with the aqueous phase S2 (form two phases) or have a lower boiling point than water and are separable therefrom by distillation.

Particularly suitable solvents S1, in addition to nitrated aromatic hydrocarbons, are in particular halogenated aliphatic or aromatic hydrocarbons. It will be appreciated that mixtures of these solvents may also be used.

Examples of particularly suitable halogenated aliphatic hydrocarbons S1 are polychlorinated or -brominated hydrocarbons having from 1 to 5 carbon atoms, in particular from 1 to 3 carbon atoms, such as dichloromethane (methylene chloride), dibromomethane, trichloromethane (chloroform), tribromo-, tetrachloro- and tetrabromomethane, 1,2-dichloro-, 1,2-dibromo-, 1,1,1-trichloro, 1,1,2-trichloro-, 1,1,1-tribromo-, 1,1,2-tribromo, 1,1,1,2-tetrachloro, 1,1,2,2-tetrachloro-, 1,1,1,2-tetrabromo- and 1,1,2,2-tetrabromoethane, and 1,2,3- and 1,1,2-trichloro-propane.

Examples of particularly suitable halogenated aromatic hydrocarbons S1 are chlorinated and brominated benzene, alkylbenzene and naphthalene, such as chloro- and bromobenzene, the isomeric dichlor-, dibromo- and trichlorobenzenes, the isomeric chloro- and bromotoluenes, and 1-chloro-, 2-chloro- and 1-bromonaphthalene.

Examples of particularly suitable nitrated aromatic hydrocarbons S1 are nitrated benzene and alkylbenzene, such as nitrobenzene and 2- and 4-nitrotoluene.

Preferred solvents S1 are chloroform, methylene chloride and chlorobenzene, of which particular preference is given to chloroform and methylene chloride.

One of the essential advantages of the process according to the invention is that the use amount of the inert organic solvent can be distinctly reduced compared to the customary procedure. Thus, generally from 1 to 50 ml, preferably from 2 to 20 ml and more preferably from 5 to 15 ml, of solvent S1 are used per g of rylenecarboximide II to be halogenated.

The sue amount of the solvent S2 (water) used in the preferred embodiment of the process according to the invention is typically from 0.2 to 5 ml, preferably from 0.5 to 2.5 ml and more preferably from 0.8 to 2 ml, per ml of solvent S1.

It is possible by the process according to the invention to prepare the halogenated rylenecarboximides of the formula I, i.e. the rylenecarboximides of the formula II, thus perylene-3,4-dicarboximides, perylene-3,4:9,10-tetracarboximides, terrylene-3,4:11,12-tetracarboximides and quaterrylene-3,4:13,14-tetracarboximides may be halogenated.

The process according to the invention has particular significance for the halogenation, preferably for the chlorination and more preferably for the bromination, of perylene-3,4-dicarboximides and in particular of terrylene-3,4:11,12-tetracarboximides and quaterrylene-3,4:13,14-tetracarboximides.

With the aid of the process according to the invention, it is possible in particular to selectively prepare the relatively highly halogenated rylenecarboximides. For example, the perylene-3,4-dicarboximides may be up to pentabrominated, preferably tribrominated, the terrylene-3,4:11,12-tetracarboximides may be up to hexabrominated, preferably tetrabrominated, and the quaterrylene-3,4:13,14-tetracarboximides may be up to octabrominated, preferably tetrabrominated and more preferably hexabrominated.

All alkyl groups occurring in the formulae I and II may be straight-chain or branched. When the alkyl groups are substituted, they generally bear 1 or 2 substituents.

Cycloalkyl groups and aromatic radicals which are substituted may generally have up to 3, preferably 1 or 2, of the substituents mentioned.

Specific examples of suitable R, R', $R^1$ and $R^2$ radicals (or their substituents) are as follows:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

methoxymethyl, 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9- trioxaundecyl, 3,6,9-trioxadodecyl, 3,6,9,12-tetraoxatridecyl and 3,6,9,12-tetraoxatetradecyl;

methylthiomethyl, 2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminoproyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

(1-ethylethylidene)aminoethylene, (1-ethylethylidene)aminopropylene, (1-ethylethylidene)aminobutylene, (1-ethylethylidene)aminodecylene and (1-ethylethylidene)aminododecylene;

propan-2-on-1-yl, butan-3-on-1yl, butan-3-on-2-yl and 2-ethylpentan-3-on-1-yl;

2-methylsulfoxidoethyl, 2-ethylsulfoxidoethyl, 2-propylsulfoxidoethyl, 2-iospropylsulfoxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl, and 4-butylsulfoxidobutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl, 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl, 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

cyanomethyl, 2-cyanoethyl, 3-cyanopropyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl, 2-, 3- and 4-nitrobutyl; methoxy, ethoxy, propoxy, isopropoxy, butyoxy, isobutoxy, sec-butoxy, tert-butoxy, pentoxy, isopentoxy, neopentoxy, tert-pentoxy and hexoxy;

methylthio, ethylthio, propylthio, isopropylthio, butylthio, isobutylthio, sec-butylthio, tert-butylthio, pentylthio, isopentylthio, neopentylthio, tert-pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8-, and 9-decynyl, 1-, 2-, 3-, 4-, 5-, 6-, 7-, 8-, 9-, 10-, and 11-dodecynyl, 1-, 2-, 3-, 4-, 5-, 6-, 7-, 8-, 9-, 10-, 11-, 12-, 13-, 14-, 15, 16- and 17- octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8-, and 9-decenyl, 1-, 2-, 3-, 4-, 5-, 6-, 7-, 8-, 9-, 10-, and 11-dodecenyl, 1-, 2-, 3-, 4-, 5-, 6-, 7-, 8-, 9-, 10-, 11-, 12-, 13-, 14-, 15, 16- and 17- octadecenyl;

methylamino, ethylamino, propylamino, isopropylamino, butylamino, isobutylamino, pentylamino, hexylamino, dimethylamino, methylethylamino, diethylamino, dipropylamino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, declaminocarbonyl and phenylaminocarbonyl;

methoxycarbonyl, ethoxycarbonyl, propoxycarbonyl, isopropoxycarbonyl, hexoxycarbonyl, dodecloxycarbonyl, octadecloxycarbonyl, phenoxycarbonyl, (4-tert-butylphenoxy)carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecloxysulfonyl, octadecloxysulfonyl, phenoxysulfonyl, 1- and 2-naphthyloxysulfonyl, (4-tert-butylphenoxy)sulfonyl and (4-chlorophenoxy)sulfonyl;

diphenylphosphino, di-(o-tolyl)phosphino and diphenylphosphinoxido;

chlorine, bromine and iodine;

methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, tert-pentylsulfonyl, hexylsulfonyl, heptylsulfonyl, octylsulfonyl, 2-ethylhexylsulfonyl, nonylsulfonyl, decylsulfonyl, 3-propylheptylsulfonyl, dodecylsulfonyl and octadecylsulfonyl;

aminosulfonyl, N,N-dimethylaminosulfonyl, N,N-diethylaminosulfonyl, N,N-dipropylaminosulfonyl, N,N-diisopropylaminosulfonyl, N,N-dibutylaminosulfonyl, N,N-diisobutylaminosulfonyl, N-N-di-sec-butylaminosulfonyl, N,N-di-tert-butylaminosulfonyl, N,N-dipentylaminosulfonyl, N,N-dihexylaminosulfonyl, N,N-diheptylaminosulfonyl, N,N-dioctylaminosulfonyl, N,N-dinonylaminosulfonyl, N,N-didecylaminosulfonyl, N,N-didodecylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert.-butylphenyl) octadecylaminosulfonyl and N,N-bis(4-chlorophenyl)aminosulfonyl;

phenylazo, 2-naphthylazo, 2-pyridylazo and 2-pyrimidylazo;

phenyl, 1- and 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-qunioliny1, 2-benzoxazolyl, 2-benzothiazolyl, 5-benzothiadiazolyl, 2- and 5-benzimidazolyl and 1- and 5-isoquinolyl;

2-, 3- and 4-methylphenyl, 2,3-, 2,4-, 2,5-, 3,5- and 2,6-dimethylphenyl, 2,4,6-trimethylphenyl, 2-, 3- and 4-ethylphenyl, 2,3-, 2,4-, 2,5-, 3,5- and 2,6-diethylphenyl, 2,4,6-triethylphenyl, 2-, 3- and 4-propylphenyl, 2,3-, 2,4-, 2,5-, 3,5- and 2,6-dipropylphenyl, 2,4,6-tripropylphenyl, 2-, 3- and 4-isopropylphenyl, 2,3-, 2,4-, 2,5-, 3,5- and 2,6-diisopropylphenyl, 2,4,6-triisopropylphenyl, 2-, 3- and 4-butylphenyl, 2,3-, 2,4-, 2,5-, 3,5- and 2,6-dibutylphenyl, 2,4,6-tributylphenyl, 2-, 3- and 4-isobutylphenyl, 2,3-, 2,4-, 2,5-, 3,5- and 2,6-diisobutylphenyl, 2,4,6-triisobutylphenyl, 2-, 3- and 4-sec-butylphenyl, 2,3-, 2,4-, 2,5-, 3,5- and 2,6-di-sec-butylphenyl and 2,4,6-tri-sec-butylphenyl, 2-, 3- and 4-tert-butylphenyl, 2,3,- 2,4-, 2,5-, 3,5- and 2,6-di-tert-butylphenyl, 2,4,6-tri-tert-butylphenyl; 2-, 3- and 4-methoxyphenyl, 2,3-, 2,4-, 2,5-, 3,5- and 2,6-dimethoxyphenyl, 2,4,6-trimethoxyphenyl, 2-, 3- and 4-ethoxyphenyl, 2,3-, 2,4-, 2,5-, 3,5- and 2,6-diethoxyphenyl, 2,4,6-triethoxyphenyl, 2-, 3- and 4-propoxyphenyl, 2,3-, 2,4-, 2,5-, 3,5- and 2,6-dipropoxyphenyl, 2-, 3- and 4-isopropoxyphenyl, 2,3-, 2,4-, 2,5-, 3,5- and 2,6-diisopropoxyphenyl and 2-, 3- and 4-butoxyphenyl; 2-, 3- and 4-chlorophenyl, and 2,3-, 2,4-, 2,5-, 3,5- and 2,6-dichlorophenyl; 2-, 3- and 4-hydroxyphenyl and 2,3-, 2,4-, 2,5-, 3,5- and 2,6-dihydroxyphenyl; 2-, 3- and 4-cyanophenyl, 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminopheny, 3- and 4-propionylaminophenyl and 3- and 4-butyrylaminophenyl, 3- and 4-N-phenylaminophenyl, 3- and 4-N-(o-tolyl)-aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)-aminophenyl, 3- and 4-(2-pyrimidyl)aminophenyl and 4-(4-pyrimidyl)aminophenyl; 3- and 4-methylsulfonylphenyl, 3- and 4-ethylsulfonylphenyl, 3- and 4-propylsulfonylphenyl, 3- and 4-isopropylsulfonylphenyl, 3- and 4-butylsulfonylphenyl, 3- and 4-isobutylsulfonylphenyl, 3- and 4-(sec-butylsulfonyl)phenyl, 3- and 4-(tert-butylsufonyl)phenyl, 3- and 4-pentylsulfonylphenyl, 3- and 4-isopentylsulfonylphenyl, 3- and 4-neopentylsulfonylphenyl, 3- and 4-(tert-pentylsulfonyl)phenyl, 3- and 4-hexylsulfonylphenyl, 3- and 4-heptylsulfonylphenyl, 3- and 4-octylsulfonylphenyl, 3- and 4-(2-ethylhexyl)sulfonylphenyl, 3- and 4-nonylsulfonylphenyl, 3- and 4-decylsulfonylphenyl, 3- and 4-(3-propylheptyl)sulfonylphenyl, 3- and 4-dodecylsulfonylphenyl and 3- and 4-octadecylsulfonylphenyl: 3- and 4-dimethylaminosulfonylphenyl, 3- and 4-diethylaminosulfonylphenyl, 3- and 4-methylethylaminosulfonylphenyl, 3- and 4-dipropylaminosulfonylphenyl, 3- and 4-diisopropylaminosulfonylphenyl, 3- and 4-dibutylaminosulfonylphenyl, 3- and 4-diisobutylaminosulfonylphenyl, 3- and 4-di-sec-butylaminosulfonylphenyl, 3- and 4-di-tert-butylaminosulfonylphenyl, 3- and 4-dipentylaminosulfonylphenyl, 3- and 4-dihexylaminosulfonylphenyl, 3- and 4-diheptylaminosulfonylphenyl, 3- and 4-dioctylaminosulfonylphenyl, 3- and 4-dinonylaminosulfonylphenyl, 3- and 4-didecylaminosulfonylphenyl and 3- and 4-didodecylaminosulfonylphenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl, 4-(5-pyrimidylazo)phenyl;

cyclopropyl, cyclobutyl, cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl, 3-, 4- and 5-propylcyclooctyl, 3- and 4hydroxycyclohexyl, 3- und 4-nitrocyclohexyl und 3- und 4-chlorocyclohexyl;

1-, 2- and 3-cyclopentenyl, 1-, 2-, 3- and 4-cyclohexenyl, 1-, 2- and 3-cycloheptenyl and 1-, 2-, 3- und 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

dipropylaminosulfonyl, diisopropylaminosulfonyl, dibutylaminosulfonyl, diisobutylaminosulfonyl, di-sec-butylaminosulfonyl, di-tert-butylaminosulfonyl, dipentylaminosulfonyl, dihexylaminosulfonyl, diheptylaminosulfonyl, dioctylaminosulfonyl, dinonylaminosulfonyl, didecylaminosulfonyl, and didodecylaminosulfonyl.

The halogenation is effected by reacting with the elemental halogen, which is intended to refer in accordance with the invention not only to elemental chlorine, bromine and iodine, but also to interhalogens such as iodine chloride.

Preferred halogens are chlorine and bromine, of which bromine is particularly preferred.

Per mole of rylenecarboximide II to be halogenated, generally from 3 to 50 mol, preferably from 5 to 30 mol, of halogen are used.

If desired, the halogen may be added in portions during the reaction. Halogen losses may be prevented by working in a closed system (autoclave).

For catalyzation of the chlorination and bromination, iodine may be added, but this not necessary in most cases. When iodine is added, the amounts are appropriately from 0.1 to 10 mol %, based on the halogen.

The reaction temperature is generally from 5 to 85° C., preferably 20 to 65° C.

In process technology terms, the procedure in the process according to the invention may be according to various variants.

In a preferred embodiment, the halogenation is carried out with stirring in a biphasic mixture of organic solvent S1 and aqueous phase S2.

The solvent phase S1 which comprises the halogen to a very great extent and in which the rylenecarboximide II to be brominated is dissolved, wetted or suspended is permanently in contact here with the aqueous phase S2, so that the hydrogen halide formed during the reaction is extracted continuously from the solvent phase S1 by washing.

If desired, the aqueous phase S2 may be removed during the reaction and exchanged for a fresh aqueous phase S2.

In this embodiment, the boiling point of the organic solvent S1 is not subject to any restriction. It merely has to be ensured that solvents S1 and S2 do not mix, i.e. two phases are formed.

This first embodiment of the process according to the invention is especially suitable for the halogenation of perylene-3,4-dicarboximides and terrylene-3,4:11,12-tetracarboximides.

In a further preferred embodiment of the process according to the invention, the halogenation is undertaken in the solvent S1 and this is contacted repeatedly with the solvent S2 and the hydrogen halide formed is withdrawn in this way.

This embodiment is based on the better solubility of the halogenated imides and is therefore preferentially suitable for the halogenation of quaterrylene-3,4:13,14-teracarboximides.

The halogenation is effected here on the rylenecarboximide II suspended in the solvent S1, and stirring is not necessary. The halogenated rylenecarboximide I dissolved in the solvent S1 is repeatedly removed by filtration from rylenecarboximide II which is yet to be converted. The organic filtrate (solvent S1, bromine, halogenated product and hydrogen halide) is then extracted by washing with aqueous phase S2 to remove the hydrogen halide, removed and sent back to the residue. If desired, the rylenecarboximide II and the bromine can be added in portions.

The removal of the organic phase L1 from the washing water L2 may be effected in various ways.

One removal variant is the separation of the liquid phases directly after the filtration or after a certain continued stirring time. In the latter case, rylenecarboximide which has not yet been fully halogenated can be halogenated further to give the target product.

However, the removal may also be effected by distilling off solvent S1 and bromine. In this variant, the solvent S1 has to have a lower boiling point than the aqueous phase S2 and thus be separable by distillation from water.

The reaction mixture (of the organic phase S1 which comprises the halogenation product and halogen residues) may be worked up in such a way that the halogen is initially removed by bubbling it out, then the solvent S1 is substantially distilled off and the halogenation product is filtered off.

For further purification, the product which has been filtered off may be washed with water and aqueous solutions of reducing agents. The reducing agent reduces remaining halogen traces to halide. Suitable reducing agents are, for example, dithionites, thioshlfates, sulfites, hydrogensulfites, nitrites and formates. In some cases (for example in the case of the dithionite sand thiosulfates), the use of alkali solutions may be appropriate.

However, it is also possible to treat the organic phase comprising the halogenation product, if desired after preceding bubbling-out, with nitrogen for example, with aqueous reducing agent solutions to remove remaining halogen traces, and subsequently to distill off the solvent.

With the aid of the process according to the invention, the halogenated rylenecarboximides I may be prepared in high yield (generally about 90%) and high purify (typically from 75 to 100%) in a simple manner from a process technology point of view. The resulting products are notable in that they comprise overhalogenated fractions only in traces (typically below 5%) and halogenation outside the rylene ring virtually does not occur. Underhalogenation may of course be substantially prevented by a sufficient reaction time.

EXAMPLES

Example 1

20.0 g (21 mmol) of N,N'-bis(2,6-diisopropylphenyl)quaterrylene-3,4:13,14-tetracarboximide were introduced into a glass fiber sleeve for a Soxhlett apparatus. 130 ml of chloroform, 105 ml of water and 18.9 ml (370 mmol) of bromine were introduced into the distillation flask of the Soxhlett apparatus. The contents of the distillation flask were then heated to reflux. A mixture of chloroform and bromine distilled off and wetted the solid in the sleeve. After the sleeve had emptied, a mixture of chloroform, bromine, and brominated product ran off into the distillation flask. The chloroform was extractively washed by the water in the distillation flask and brought again to distillation together with the bromine. A further 11.4 ml (220 mmol) of bromine were added in three portions. After a reaction time of 70 hours, remaining bromine and chloroform were distilled off.

The residue in the distillation flask was filtered off, washed with water and 20% by weight aqueous sodium sulfite solution, and dried under reduced pressure.

24.6 g of N,N'-bis(2,6-diisopropylphenyl)hexabromoquaterrylene-3,4:13,14-tetracarboximide ($R_f$ (toluene)=0.17) were obtained (82% yield).

Comparative Example 1C

N,N'-Bis(2,6-diisopropylphenyl)quaterrylene-3,4:13,14-tetracarboximide was brominated analogously in the same apparatus, but in the absence of water.

In addition to the desired hexabrominated product, distinct amounts of overbrominated products were obtained and are recognizable in the thin-layer chromatogram by the low polarity (higher $R_f$ values): ($R_f$(toluene)=0.17; 0.33; 0.61.

Example 2

19.1 g (0.023 mol) of N,N'-bis(2,6-diisopropylphenyl)terrylene-3,4:11,12-tetracarboximide were dissolved in 250 ml of chloroform and admixed with 500 ml of water. Subsequently, 18.6 ml (0.36 mol) of bromine were added slowly within 2 min. After stirring at 40° C. for 5 hours and stirring at room temperature for 15 hours, the remaining bromine and chloroform were distilled off.

The residue was filtered off, washed with water and 20% by weight aqueous sodium sulfite solution, and dried under reduced pressure.

26.1 g of N,N'-bis(2,6-diisopropylphenyl)tetrabromoterrylene-3,4:11,12-tetracarboximide ($R_f$ (methylene chloride) =0.75; bromine content: 27.6% (found); 27.8% (calc.)) were obtained (99% yield).

Example 3

5.0 g (10 mmol) of N-(2,6-diisopropylphenyl)perylene-3,4-dicarboximide were dissolved in 65 ml of chloroform and admixed with 130 ml of water. Subsequently, 7 ml (130 mmol) of bromine were added and the mixture was heated to 30° C. After stirring at this temperature for 5 hours and stirring at room temperature for a further 60 hours, the remaining bromine was removed by bubbling-out with nitrogen.

organic and aqueous phase were separated. The organic phase was then extracted by shaking twice with 20% by weight aqueous alkali sodium thiosulfate solution, dried over magnesium sulfate and concentrated.

7.0 g of N-(2,6-diisopropylphenyl)tribromoperylene-3,4-dicarboximide were obtained (98% yield). This comprises two isomers in a ratio of about 1:6: $R_f$(toluene)=0.25; 0.36.

Comparative Example 3C 10.0 g (20 mmol) of N-(2,6-diisopropylphenyl)perylene-3,4-dicarboximide were dissolved in 400 ml of chloroform and, after addition of 50 ml (975 mmol) of bromine, heated to 70° C. for 6 h. The workup was effected analogously to example 3.

In addition to the desired tribrominated product, distinct amounts of tetrabrominated product were obtained and are recognizable in the thin-layer chromatogram by the lower polarity (higher $R_f$ values): $R_f$ (toluene)=0.25; 0.36; 0.50; 0.58.

What is claimed is:

1. A process for preparing halogenated rylenecarboximides of the general formula I

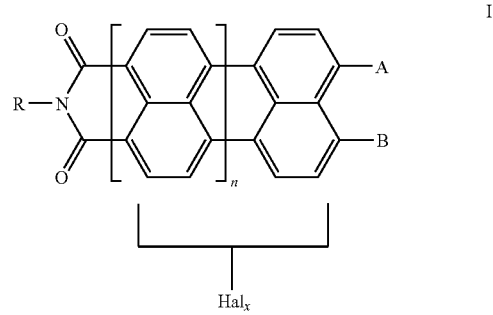

in which the variables are each defined as follows:

A, B together are an imide radical of the formula

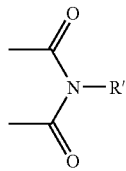

or, in the case that n is 1, A and B are each Hal or one radical is Hal and the other radical is hydrogen;

R, R' are each independently:

hydrogen;

(1) $C_1$-$C_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by:

(i) $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(ii) aryl or hetaryl, to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or hetaryl, each of which may be substituted by $C_1$-$C_{18}$-alkyl, $C_1$-$C_{12}$-alkoxy, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(iii) $C_3$-$C_8$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties and to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$;

(iv) a -U-aryl radical which may be mono- or polysubstituted by the above radicals specified as substituents for the aryl radicals (ii), where U is an —O—, —S—, —NR$^1$—, —CO—, —SO— and/or —SO$_2$— moiety;

(2) $C_3$-$C_8$-cycloalkyl, to which may be fused further saturated or unsaturated 5- to 7-membered rings whose carbon skeleton may be interrupted by one or more —O—, —S—, —NR$^1$—, —N=CR$^1$—, —CR$^1$=CR$^1$—, —CO—, —SO— and/or —SO$_2$— moieties, where the entire ring system may be mono- or polysubstituted by the (i), (ii), (iii), (iv) radicals, and/or (v) $C_1$-$C_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by: $C_1$-$C_{12}$-alkoxy, $C_1$-$C_6$-alkylthio, —C≡CR$^1$, —CR$^1$=CR$^1{}_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$ and/or —POR$^2$R$^3$, aryl and/or saturated or unsaturated $C_4$-$C_7$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties, where the aryl and cycloalkyl radicals may each be mono- or polysubstituted by $C_1$-$C_{18}$-alkyl and/or the above radicals specified as substituents for alkyl;

(3) aryl or hetaryl, to which may be fused further saturated or unsaturated 5- to 7-membered rings whose carbon skeleton may be interrupted by one or more —O—, —S—, —NR$^1$—, —N=CR$^1$—, —C≡C—, —CR$^1$=CR$^1$—, —CO—, —SO— and/or —SO$_2$— moieties, where the entire ring system may be substituted by the (i), (ii), (iii), (iv), (v) radicals, and/or aryl- and/or hetarylazo, each of which may be substituted by $C_1$-$C_{10}$-alkyl, $C_1$-$C_6$-alkoxy and/or cyano;

$R^1$ is hydrogen or $C_1$-$C_{18}$alkyl, where the $R^1$ radicals may be the same or different when they occur more than once;

$R^2$, $R^3$ are each independently hydrogen;

$C_1$-$C_{18}$-alkyl whose carbon chain may be interrupted by one or more —O—, —S—, —CO—, —SO— and/or —SO$_2$— moieties and which may be mono- or polysubstituted by $C_1$-$C_{12}$-alkoxy, $C_1$-$C_6$-alkylthio, hydroxyl, mercapto, halogen, cyano, nitro and/or —COOR$^1$;

aryl or hetaryl, to each one of which may be fused further saturated or unsaturated 5- to 7-membered rings whose carbon skeleton may be interrupted by one or more —O—, —S—, —CO— and/or —SO$_2$- moieties, where the entire ring system may be mono- or polysubstituted by $C_1$-$C_{12}$-alkyl and/or the above radicals specified as substituents for alkyl;

Hal is chlorine, bromine or iodine;

n is 1, 2 or 3;

x is from 1 to 8, by reacting a rylenecarboximide of the general formula II

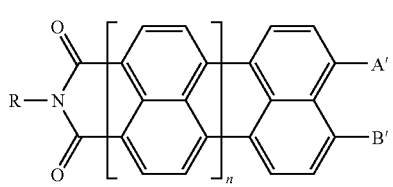

in which the A' and B' radicals are an imide radical of the formula

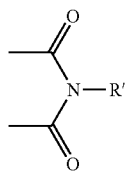

or, in the case that n is 1, are also each hydrogen with elemental halogen in the presence of an inert organic solvent S1, which comprises continuously withdrawing the hydrogen halide formed in the course of the reaction from the solvent S1.

2. The process according to claim 1, which is used to prepare halogenated rylenecarboximides of the formula I in which the variables are each defined as follows:

R, R' are each independently hydrogen;

$C_1$-$C_{30}$-alkyl whose carbon chain may be interrupted by one or more —O—, —S—, —NR$^1$—, —CO— and/or —SO$_2$— moieties and which may be mono- or polysubstituted by cyano, $C_1$-$C_6$-alkoxy, aryl which may be substituted by $C_1$-$C_{18}$-alkyl or $C_1$-$C_6$-alkoxy, and/or a 5- to 7-membered heterocyclic radical which is bonded via a nitrogen atom and may comprise further heteroatoms and be aromatic;

$C_5$-$C_8$-cycloalkyl whose carbon skeleton may be interrupted by one or more —O—, —S— and/or —NR$^1$— moieties and/or which may be mono- or polysubstituted by $C_1$-$C_6$-alkyl;

aryl or hetaryl, each of which may be mono- or polysubstituted by $C_1$-$C_{18}$-alkyl, $C_1$-$C_6$-alkoxy, cyano, halogen, —CONHR$^2$, —SO$_2$R$^2$, —SO$_2$NR$^2{}_2$ and/or aryl- or hetarylazo, each of which may be substituted by $C_1$-$C_{10}$-alkyl, $C_1$-$C_6$-alkoxy or cyano;

$R^1$ is hydrogen or $C_1$-$C_6$-alkyl;

$R^2$ is hydrogen; $C_1$-$C_{18}$-alkyl; aryl or hetaryl, each of which may be substituted by $C_1$-$C_6$-alkyl, $C_1$-$C_6$-alkoxy, halogen, hydroxy, carboxy or cyano.

3. The process according to claim 1, wherein the solvent S1 is contacted with a solvent S2 by which the hydrogen halide is extracted from the solvent S1 and which does mix with the solvent S1 and/or has a higher boiling point than the solvent S1 and can be separated from it by distillation.

4. The process according to claim 3, wherein the solvent S2 used is water or an aqueous solution of inorganic oxidizing agents and/or inorganic bases.

5. The process according to claim 3, wherein the halogenation is carried out with stirring in a biphasic mixture of solvent S1 and S2.

6. The process according to claim 3, wherein the halogenation is undertaken in the solvent S1 which is contacted repeatedly with the solvent S2 and the hydrogen halide formed is removed in this way.

7. The process according to claim 1, wherein the solvent S1 used is a halogenated aliphatic or aromatic or nitrated aromatic hydrocarbon.

8. The process according to claim 1, wherein the solvent S1 used is chloroform, methylene chloride or chlorobenzene.

9. The process according to claim 1, wherein the rylenecarboximides of the formula II used are perylene-3,4-dicarboximides, terrylene-3,4:11,12-tetracarboximides or quaterrylene-3,4:13,14-tetracarboximides.

10. The process according to claim 1, wherein the halogen used is bromine.

11. The process according to claim 1, which is used to prepare tribromoperylene-3,4-dicarboximides, tetrabromoterrylene-3,4:11,12-tetracarboximides and hexabromoquaterrylene-3,4:13,14-tetracarboximides.

\* \* \* \* \*